United States Patent [19]

Anaebonam et al.

[11] Patent Number: 5,626,879
[45] Date of Patent: May 6, 1997

[54] TERFENADINE ORAL GRANULES

[75] Inventors: Aloysius O. Anaebonam, Burlington, Mass.; Abdel A. Fawzy, Nashua, N.H.; Emmett Clemente, Manchester, Mass.

[73] Assignee: Ascent Pharmaceuticals, Inc., Billerica, Mass.

[21] Appl. No.: 537,538

[22] Filed: Oct. 2, 1995

Related U.S. Application Data

[63] Continuation-in-part of Ser. No. 368,421, Jan. 4, 1995, Pat. No. 5,455,049.
[51] Int. Cl.$^6$ .................................... A61K 9/16
[52] U.S. Cl. .................... 424/489; 424/493; 424/499; 424/464
[58] Field of Search ..................... 424/489, 493, 424/464, 499

[56] References Cited

U.S. PATENT DOCUMENTS 5,250,529  10/1993  Theoharides ..................... 514/255

*Primary Examiner*—Thurman K. Page
*Assistant Examiner*—Sharon Howard
*Attorney, Agent, or Firm*—Welsh & Katz, Ltd.

[57] ABSTRACT

The present invention contemplates a dry, granular terfenadine composition. That composition comprises (i) particulate terfenadine and (ii) a polyethylene oxide-polypropylene oxide-polyethylene oxide block copolymer having an HLB number of 24 that is a wetting agent for the terfenadine that are dry-blendedly dispersed onto (iii) spray-dried sorbitol particles that are loosely packed, randomly oriented filamentary crystals having pores that entrap the particulate terfenadine and wetting agent upon the dry-blended dispersal. The weight ratio of particulate terfenadine to the block copoymer is about 1:1 to about 1:5:1, and the weight ratio of terfenadine to the spray-dried sorbitol is about 1:4 to about 1:10. The composition is free-flowing and is substantially free from the taste of solubilized terfenadine when placed on the human tongue in dry form or when dispersed in water and tasted within about five minutes of said dispersal. A preferred composition further includes dry-blendedly admixed polyvinylpyrrolidone present in an amount of about 0.5 to about 5 weight percent of the total composition. Flavorants can also be present.

20 Claims, No Drawings

TERFENADINE ORAL GRANULES

CROSS-REFERENCE TO RELATED APPLICATION

This is a continuation-in-part of application Ser. No. 08/368,421, filed Jan. 4, 1995 and now U.S. Pat. No. 5,455,049, whose disclosures are incorporated by references.

TECHNICAL FIELD

The present invention relates to orally administrable antihistamine-containing granules, and more particularly to an orally administrable, pleasant tasting particulate form of terfenadine that when applied to the tongue is substantially free of the taste of solubilized terfenadine.

BACKGROUND ART

Terfenadine is a well-known antihistamine that is a selective antagonist of the histamine $H_1$-receptor. Terfenadine lacks sedative properties. This particularly effective drug has a particularly offensive taste when dissolved and is consequently formatted for oral administration as a pill or tablet that minimizes that offensive taste.

Although provision in a tablet form overcomes the problem of offensive taste for this valuable medicament for most of the adult population that uses terfenadine, many adults and many children have difficulty swallowing the pills or tablets or cannot swallow them, and thereby do not benefit from terfenadine.

The disclosure that follows illustrates one solution to the problem of terfenadine delivery that is applicable to adults and children that cannot swallow capsules or have difficulty doing so, as well as an alternative delivery mode for the general population.

BRIEF SUMMARY OF THE INVENTION

A dry, granular terfenadine composition is contemplated. In one embodiment the composition comprises (i) particulate (powdered or micronized) terfenadine and (ii) a polyethylene oxide-polypropylene oxide-polyethylene oxide block copolymer having an HLB number of 24 that is a wetting agent for the terfenadine. Those components are dry-blendedly dispersed into (iii) spray-dried sorbitol granules that are loosely packed, randomly oriented filamentary crystals having pores that entrap the particulate terfenadine and wetting agent upon the dry-blended dispersal. The weight ratio of particulate terfenadine to block copolymer is about 1:1 to about 1.5:1, and the weight ratio of terfenadine to spray-dried sorbitol is about 1:4 to about 1:10. The composition is free-flowing and is substantially free from the taste of solubilized terfenadine when placed on the human tongue in dry form or when dispersed in water and tasted within about five minutes of said dispersal. A composition in one preferred embodiment contains about 8 to about 12 weight percent particulate terfenadine, about 5 to 10 weight percent polyethylene oxide-polyethylene oxide-polyethylene oxide block copolymer, about 35 to about 70 weight percent of the above sorbitol granules with the remainder being a flavorant such as maltodextrin and can also include polyvinylpyrrolidone (RVP). In another preferred embodiment, an above three part composition further includes dry-blendedly admixed polyvinylpyrrolidone that is present in an amount of about 0.5 to about 5 weight percent of the total composition. A contemplated granular terfenadine composition typically contains an antihistaminic dose of terfenadine.

A more complex composition is preferred for many uses. Such a preferred composition comprises (a) a mixture of:
  (i) about 0.20 to about 25 parts by weight particulate (powdered or micronized) terfenadine, and
  (ii) about 0.1 to about 15 parts by weight a polyethylene oxide-polypropylene oxide-polyethylene oxide block copolymer (Poloxamer) having an HLB number of about 24 that is a wetting agent for the terfenadine;

Those components are jointly dry-blendedly dispersed into:

(b) about 10 to about 80 parts by weight spray-dried sorbitol particles. The particles are loosely packed, randomly oriented filamentary crystals having pores that entrap the particulate terfenadine particles and wetting agent upon dry-blended dispersal. The three blended components are further dry blended with (c) about 0.5 to about 10 parts by weight dry polyvinylpyrrolidone (PVP);

(d) zero to about 5 parts by weight dry microcrystalline cellulose that includes sodium carboxymethylcellulose; and (e) a dry flavorant that can be absent or present in an amount sufficient to provide a desired taste to the granular composition.

The resulting composition is free-flowing and granular, and is substantially free from the taste of solubilized terfenadine when placed on the human tongue in dry form, compressed into chewable tablets or when dispersed in water and tasted within about five minutes of the dispersal.

The present invention has several benefits and advantages.

One benefit is that the terfenadine oral powder disclosed can be taken by those persons that have difficulty swallowing usually supplied pills or tablets, or cannot so swallow without experiencing the offensive taste usually associated with solubilized terfenadine.

An advantage of the invention is that the terfenadine oral granules can also be dispersed in foods or aqueous liquids and consumed without exhibiting the usual offensive taste of solubilized terfenadine.

Another benefit of the invention is that the powdered composition, once placed onto the tongue, disperses almost immediately, without having a gritty or other noticeable residue.

Another advantage of the invention is that use of dry granulation procedures provides enhanced efficiency in manpower and energy usage compared to a liquid mixing procedure in that no drying step is required.

Still further benefits and advantages of the present invention will be apparent to the worker of ordinary skill from the disclosure that follows.

DETAILS DESCRIPTION OF THE INVENTION

The present invention contemplates a free-flowing granular form of terfenadine that is pleasant tasting, substantially free from the usual taste of solubilized terfenadine, and is designed to be taken orally as by administration directly into the mouth, chewed as chewable tablets or upon reconstitution in a small amount of water or in food.

A contemplated composition can be used as a three part or a four part concentrate that is itself used as a basis for a further product that is ultimately sold to a consumer, or a three or four part granular composition can itself be sold for consumption with or without further ingredients such as a flavorant. A contemplated three part composition contains terfenadine, Poloxamer and sorbitol INSTANT™, whereas a contemplated four part composition contains those three ingredients and further contains PVP.

A preferred granular composition is adapted for oral ingestion and can be used as oral granules for direct application into a user's mouth contains a particulate terfenadine to sorbitol INSTANT™ weight ratio of about 1:4 to 1:10, and a weight ratio of particulate terfenadine to Poloxamer of about 1:1 to about 1.5:1. The PVP present in a four part granular composition need only be present in amount of about 0.5 to about 5 weight percent of the total composition. An antihistaminic dosage of terfenadine is preferably present.

One preferred embodiment of a three part composition also includes a flavorant such as maltodextrin, sucrose, mannitol or xylitol, as are discussed in detail hereinafter. An exemplary composition contains about 8 to about 12 weight percent particulate terfenadine, about 5 to about 10 weight percent Poloxamer, about 35 to about 7 weight percent sorbitol INSTANT™, with a remaining about 15 to about 45 weight percent of the composition containing a flavorant. Addition of an above amount of PVP converts the above composition into a four part composition.

A particularly preferred composition prepared from an above four part concentrate comprises (a) a mixture of (i) about 0.20 to about 25 parts by weight of particulate terfenadine and (ii) about 0.1 to about 15 parts by weight of a polyethylene oxide-polypropylene oxide-polyethylene oxide block co-polymer having an HLB number of about 24 that is a wetting agent (dispersant) for the terfenadine;

(ii) about 10 to about 80 parts by weight, and preferably about 20 to about 40 parts by weight spray-dried sorbitol granules, a loosely packed, randomly oriented filamentary crystals having pores that entrap the terfenadine particles and wetting agent upon the dry-blended dispersal. The dry blended (a) and (b) components are further dry blended with (iii) about 0.5 to about 10 parts by weight dry polyvinylpyrrolidone;

(iv) zero to about 5 parts by weight dry microcrystalline cellulose; and (v) a dry flavorant that can be absent or present in an amount sufficient to provide a desired pleasant taste to the powdered composition.

The resulting granular composition is free-flowing and is substantially free from the taste of solubilized terfenadine when placed on the human tongue in dry form, when chewed as a chewable tablet or when dispersed in water and tasted within about five minutes of that dispersal.

A contemplated composition contains micronized or powdered (particulate) terfenadine and a spray-dried sorbitol. Those materials can be present at a weight ratio of 1:100 to about 1:2 terfenadine to sorbitol. That weight ratio is preferably about 1:20 to about 1:2, more preferably about 1:12.5 to about 1:3.5, and most preferably is about 1:10 in the order noted.

The wetting agent block co-polymer assists in dispersing the particulate terfenadine, but does not form micellular structures that solubilize the terfenadine. The wetting agent is present at about one-tenth to about an equal weight, and more preferably at about one-fifth to about one-half the weight of the micronized or powdered terfenadine, and more preferably at about one-half the weight of terfenadine.

Polyvinylpyrrolidone (PVP; povidone) that acts as a de-bittering agent to the terfenadine and secondarily can assist in building viscosity and mouth feel is present at a weight ratio of the sorbitol particles of about 1:20 to about 1:8 and more preferably at about 1:10 to about 1:4 of PVP:sorbitol.

A mixture of microcrystalline cellulose and sodium carboxymethylcellulose that acts as a suspending agent for the blended materials can also be present at zero to about 5 parts by weight. This cellulose mixture, when used, is present at a weight ratio of about 1:20 to about 1:8 relative to the sorbitol. More preferably, that weight ratio is about 1:12 to about 1:9; with a weight ratio of about 1:10 being most preferred.

The composition can also contain a flavorant that can be a single ingredient such as fructose or sucrose or both, or more complex mixtures of materials that provide a desired pleasant sweetness or other flavor than that of solubilized terfenadine itself. The composition is substantially free from a solubilized terfenadine taste and has a pleasant, non-medicinal taste.

The composition is also free-flowing in that its individual particles tend not to clump together or agglomerate even when in the mouth or stirred in an amount of water sufficient to form a watery suspension, as compared to a paste or cream. The dry composition therefore flows freely when poured from one vessel to another.

Turning more specifically to the individual ingredients, the terfenadine used herein is terfenadine USP that has been finely comminuted into a fine powder or micron-sized particles. The terfenadine is therefore often referred to herein as particulate to highlight its small particle size, and at other times hereinafter that material is called terfenadine. The micronized terfenadine is sized so that 100 percent of the particles are less than 10 μm, and at least 85 percent are smaller than 5 μm. Typical bulk densities for this material are about 0.1 to about 0.5 g/ml. The powdered terfenadine has an average size of about 10 μm to about 50 μm, with an average size of about 30 μm being preferred.

Micronized and powdered terfenadine are available from several commercial sources. Illustrative sources include CiLag AG Schalfhausen, Switzerland (Zetapharm, Inc. of New York, N.Y.); and Erregirre Industrial Chimiea, SpA, Italy (Flavine International Inc. of Closter, N.J.).

The usual antihistaminic dosage of terfenadine for adults and children over 13 years of age is 60 mg twice each day. For younger children, the dosage is usually about 15–30 mg twice each day.

As used here, a single dose of a granular or chewable tablet composition having a total mass of 0.5, 1 or 2 grams is designed to carry the entire antihistaminic amount of terfenadine. As a consequence, the amounts of ingredients other than micronized or powdered terfenadine are based upon the amount of terfenadine preferably being calculated to be a dose of about 15, 30 or 60 mg. It should also be understood that less than the usual antihistaminic amount can be used in a single dose with several doses being supplied at about the same time or within about one hour of each other to provide an antihistaminic amount of terfenadine.

Thus, a granular or chewable tablet composition, when viewed only as a composition, need only define relative amounts by parts or other ratios of each ingredient to another ingredient or ingredients. However, when used to supply an antihistaminic amount of terfenadine, or contemplated in a process for use or treatment, total amounts of ingredients are considered.

In a given composition, particulate (micronized or powdered) terfenadine is present at about 1 to about 20 parts.

Preferably, the micronized terfenadine is present at about 2 to about 10 parts, and most preferably at about 3 parts by weight. The powdered terfenadine, usually used for chewable tablets or other direct to the tongue products such as oral granules, is preferably present at about 5 to about 15 parts, and most preferably at about 8 to about 12 parts by weight.

A contemplated polyethylene oxide-polypropylene oxide-polyethylene oxide block copolymer wetting agent is referred to in the nomenclature of the *International Cosmetic Ingredient Dictionary*, 5th ed., Menninger et al., eds., The Cosmetic, Toiletry, and Fragrance Association, Washington, D.C. (1993) as a "Poloxamer", followed by a numerical designation. A particular Poloxamer of interest here contains polyethylene oxide blocks of about equal average length on either side of the polypropylene oxide block, with the average total molar ratio of oxyethylene to oxypropylene repeating groups in each molecule being about 5 to about 6. These materials are all solids at ambient room temperature and have an HLB of 24.

Exemplary Poloxamer wetting agent molecules are sold under the trademark PLURONIC™ polyol F-38, F-68, F-88, F-98 and F-108 for Poloxamers 108, 188, 238, 288 and 338, respectively. PLURONIC™ polyol F-68 is particularly preferred. These PLURONIC™ polyols are available from BASF Corporation of Mount Olive, N.J.

The Poloxamer is present at about one-tenth to about equal the weight of the particulate terfenadine, and preferably at about one-fifth to about one-half the weight of the particulate terfenadine, with more of the Poloxamer wetting agent being used when more particulate terfenadine is used. Lower ratios of Poloxamer are used with micronized terfenadine and higher ratios with powdered terfenadine. Thus, where the granular composition contains about 1 to about 20 parts particulate terfenadine, about 0.1 to about 20 parts, and preferably about 0.2 to about 10 parts Poloxamer wetting agent are also present. With a more preferred amount of micronized terfenadine of about 2 to about 10 parts, one uses about 1 to about 5 parts Poloxamer, and most preferably, about 1.5 parts Poloxamer are used with 3 parts micronized terfenadine. Similarly, for a preferred amount of about 5 to about 15 parts of powdered terfenadine, about 0.5 to about 15 parts Poloxamer can be used, or more preferably about 8 to about 12 parts terfenadine powder.

In terms of particulate terfenadine, the weight ratio of Poloxamer to terfenadine is about 1.5:1 to about 1:2, and more preferably about 1:1 to about 1:1.5.

The spray-dried sorbitol is a specialized product produced by E. Merck of Darmstadt, and available from EM Industries Inc. of Hawthorne, N.Y. under the trademark sorbitol INSTANT™. Sorbitol INSTANT™ is spray-dried from an aqueous solution and whereas crystalline sorbitol exhibits sharp angles, a smooth particle surface and provides a gritty texture and mouth feel when tableted, sorbitol INSTANT™ is comprised of loosely packed, randomly oriented, interwoven filamentary crystal particles. Magnification of those particles shows pore spaces within the particles and a furry-looking particle surface appearance. Any reference to "sorbitol" herein except a specific reference to the usual "crystalline sorbitol" is to sorbitol INSTANT™.

Sorbitol is known to have a high capacity to adsorb some small drug particles, with the adsorption being dependent upon particle size as well as electrostatic and Van der Waals forces. Thus, some drugs such as acetaminophen do not form adsorbates to a high degree, whereas others such as erythromycin ethylsuccinate form very concentrated adsorbates.

Two forms of sorbitol INSTANT™ are commercially available, and both can be used herein. The first is referred to as 7703 sorbitol INSTANT™ Pharma, which is preferred, and the second is referred to as 11578 sorbitol INSTANT™ P3000. Both products are soluble at 360 g/100 ml water at 40° C. and have a specific rotation, $[\alpha]_D^{20}$ (c=1, water, borato-complex) of +4.0° to +7.0°, calculated as the anhydrous material that it is.

The two materials differ in particle size and therefore bulk density. 7703 sorbitol INSTANT™ Pharma has the following particle size distribution: <212 µm (70 mesh) <5 percent, <500 µm (35 mesh) <80 percent; and >850 µm (20 mesh) <5 percent, with a bulk density of 38–46 g/100 ml and a tapped density of 45–50 g/100 ml. 11578 sorbitol INSTANT™ P3000 has the following particle size distribution: <53 µm (270 mesh) <15 percent, 53–106 µm (270–140 mesh) 15–20 percent, 106–212 µm (140–70 mesh) 40–50 percent, 212–500 µm (70–35 mesh) 20–30 percent, and >500 µm (35 mesh) <1 percent, with a bulk density of 45–55 g/100 ml and a tapped density of 51–56 g/100 ml. Sieve sizes are U.S. Standard Sieve Series.

The sorbitol is usually used in excess over the terfenadine so that when more terfenadine is present, more sorbitol INSTANT™ is used. Sorbitol INSTANT™ is responsible for the granularity of a contemplated composition. A preferred composition that contains 0.25 to about 25 parts micronized or powdered terfenadine can contain about 20 to about 40 parts sorbitol. A preferred composition containing about 2 to about 10 parts terfenadine contains about 25 to about 35 parts sorbitol INSTANT™, whereas a most preferred composition that contains about 3 parts micronized terfenadine contains about 30 parts sorbitol or about 8 to about 12 parts powdered terfenadine contains about 50 to about 65 parts sorbitol. A preferred weight ratio of sorbitol INSTANT™ to terfenadine is about 2.5:1 to about 20:1, and more preferably about 4:1 to about 10:1.

Sorbitol can also be used in greater amounts to provide bulk to the composition, as is usually the case with chewable tablets and other direct on the tongue products such as oral granules. Any excess in the amount of sorbitol over the weight ratio to terfenadine discussed hereinbefore is so used, as compared to the primary use of sorbitol INSTANT™ as a dispersing and taste-masking agent for the terfenadine.

The micronized or powdered terfenadine and block copolymer wetting agent are usually dry-blendedly dispersed into the sorbitol. That is, the first two ingredients are blended dry with each other and then with the sorbitol INSTANT™, and adhere to the sorbitol and fill its pores. Alternatively, particulate terfenadine and sorbitol can be dry blended and the Poloxamer blended to that blend or vice versa. This blending is preferably accomplished by a tumbling mixer with the fortunate result that both the terfenadine and block copolymer adhere to the sorbitol particles without greatly changing the particle size of the sorbitol except for the size increase due to the adsorption and without noticeable agglomeration of filled and coated sorbitol particles. This lack of agglomeration contributes to the free flowing character of the final granular composition.

The above dry blended components are thereafter dry blended further with dry PVP, dry microcrystalline cellulose and a dry flavorant, when used, as are discussed below.

The polyvinylpyrrolidone (PVP) is a well known item of commerce that is available in several molecular weight grades from several suppliers. A particularly preferred material is sold under the trademark KOLLIDON™ by BASF Corp. of Mount Olive, N.J. Exemplary materials are sold as KOLLIDON™ 25, 30 and 90 that have weight average molecular weights of about 25,700, 42,500 and 1,100,000, respectively. These materials are free flowing powders with particle sizes in the range of about 50 to about 250 μm. Particles smaller than 50 μm are present at less than 10 percent for all grades, and particles greater than 250 μm are less than 5 percent for KOLLIDON™ 25 and 30, and less than 20 percent for KOLLIDON™ 90. Bulk densities are about 0.40–0.50 g/ml, 0.35–0.50 g/ml and 0.40–0.50 g/ml for KOLLIDON™ 25, 30 and 90, respectively.

The highest molecular weight material, KOLLIDON™ 90, is preferred herein. This material, unexpectedly and primarily, provides a further taste-enhancing, de-bittering function to the terfenadine. Secondarily, the PVP also provides an enhanced mouthfeel when the composition is on the tongue, and additionally provides body (viscosity) when the composition is reconstituted in water.

The PVP, when present as is particularly 5 preferred, is used at a weight ratio of about 1:50 to about 1:4, at preferably at about 1:10 to about 1:4 to sorbitol. More of the PVP is used when more terfenadine and sorbitol are in the composition, except where a chewable tablet is desired, in which case the sorbitol to PVP ratio can exceed 50:1. Thus, about 20 to about 40 parts sorbitol are typically used with about 2 to about 10 parts of PVP in other than chewable tablets. More preferably, about 25 to about 35 parts sorbitol are used with about 3 to about 7 parts PVP. Most preferably, about 30 parts of sorbitol are used with about 5 parts of PVP, for other than chewable tablets where sorbitol INSTANT™ is also used as a bulking agent.

Looked at differently, the total PVP in a contemplated composition is about 0.5 to about 5 weight percent, and preferably at about 0.1 to about 5 weight percent.

A mixture of microcrystalline cellulose and sodium carboxymethylcellulose (NaCMC) can also be present also utilized in the composition as a colloidal suspending agent, particularly where a granular composition is to be dispersed in a food or aqueous liquid. In such a use, the NaCMC is present at about 0.5 to about 5 weight percent of the granular composition. The NaCMC is present at about 7 to about 20 weight percent in this mixture so the mixture is more simply referred to as microcrystalline cellulose as that material constitutes about 80 to about 93 percent of the total. This material is listed in the *U.S. Pharmacopeia National Formulary* as microcrystalline cellulose and carboxymethylcellulose sodium.

A preferred mixture is available from FMC Corporation, Philadelphia, Pa. under the trademarks AVICEL™ RC-501, RC-581, RC-591 and CL-611. These materials are solid powders that pass through a 60 mesh sieve to at least 99.9 percent and are retained on a 200 mesh sieve at not more than 40 and 35 weight percents (AVICEL™ RC-501 and RC-581, respectively), or 45 and 50 percents on a 325 mesh sieve (AVICEL™ RC-591 and CL-611, respectively). The two first designated materials typically require high shear mixing for dispersion in water, whereas the latter two materials only require moderate shear for dispersion.

AVICEL™ CL-611 is preferred herein and forms a thixotropic gel in water when present at greater than 1.2 percent. This material contains about 11 to about 19 percent NaCMC.

The microcrystalline cellulose mixture can be present at zero to about 5 parts, preferably about 0.5 to about 5 parts, and more preferably at about 1 to about 5 parts. This material is present at a weight ratio of about 1:20 to about 1:8 relative to the sorbitol. As more terfenadine and sorbitol are used, in other than a chewable tablet, more of the microcrystalline cellulose is also used. Thus, in other than chewable tablets, where about 20 to about 40 parts sorbitol are present, about 1 to about 5 parts of microcrystalline cellulose are also present. More preferably, about 25 to about 35 parts sorbitol are used with about 2 to about 4 parts microcrystalline cellulose. Most preferably, about 3 parts microcrystalline cellulose are used with about 30 parts sorbitol.

A flavorant can also be present. Most preferably, the flavorant is a sweetener that is a mixture of saccharides such as maltodextrin and sucrose, fructose, mannitol or xylitol. These flavorants can comprise about 15 to about 75 weight percent and more preferably comprise about 40 to about 60 weight percent of the final composition. In other embodiments, the flavorant can be present at about 15 to about 45 weight percent, down to only a few percent when artificial sweeteners are used, or where a product with virtually no sweetness or other taste is desired.

A preferred maltodextrin, which is a hydrolyzed cornstarch polymer having $\alpha\text{-}1\rightarrow 4$-linked D-glucose units and having a dextrose equivalent (DE) of less than or equal to about 20, is the agglomerated product sold under the trademark MALTRIN™ QD. The MALTRIN™ QD products are sold by Grain Processing Corp., Muscatine, Iowa. Products are sold under the designations QD M440, M500 and M600 that have DE values of 4–7, 9–12 and 20–23, respectively.

The preferred MALTRIN™ QD M500 has a particle size specification that requires a minimal 90 percent passage through a U.S. #20 mesh sieve screen and a maximal 10 percent passage through a U.S. #200 sieve screen. A typical particle size distribution provides 95 percent through a #20 sieve screen, 50 percent through a #60 sieve screen, 25 percent through a #100 sieve screen and 6 percent through a #200 sieve screen, U.S. Sieve Series.

These agglomerated maltodextrins have low bulk densities, e.g., MALTRIN™ QD M500 that is preferred has a bulk density of 34 g/100cc, are relatively non-friable and do not disintegrate readily in dry mixing. These materials also disperse very rapidly in water, e.g., 100 percent of a 15 weight percent mixture of MALTRIN™ QD M500 in water dissolves in one minute on mixing.

The agglomerated maltodextrin has a bland flavor that helps control sweetness and is also used as a bulking and flow control agent in the powder. On dissolution or dispersion in water, the agglomerated maltodextrin also contributes to building viscosity.

Sucrose, fructose (sugar), mannitol or xylitol in finely divided form is a principal flavorant, and provides sweetness as is well known. These materials are available from several commercial sources. An exemplary fructose is available from Roquette Corp., Gurnee, Ill.

It is preferred to use both the agglomerated maltodextrin and either sucrose or fructose as the flavorant, or part of the flavorant. It is also preferred to use about twice the amount of sugar as agglomerated maltodextrin. The combined amount of maltodextrin and sugar is used at about twice the amount of sorbitol.

Broadly, where sorbitol is present at about 10 to about 80 parts by weight or preferably about 20 to about 40 parts, the agglomerated maltodextrin can be present at 10 to about 80 parts or preferably at about 10 to about 40 parts, and the sugar at about 10 to about 50 parts. With a preferred amount of about 25 to about 35 parts sorbitol, about 15 to about 25 parts agglomerated maltodextrin and about 30 to about 40 parts sugar are used. With the most preferred 30 parts sorbitol, about 20 parts agglomerated maltodextrin are used with about 37.5 parts sugar.

Artificial sweeteners such as aspartame, saccharin and cyclamates can also be used as flavorants in addition to or as replacements for the above flavorants. Dried fruit flavors such as orange and lemon flavors and other well known dry flavorants can also be used in place of some or all of the above flavorants.

When used as chewable tablets, a contemplated composition usually utilizes powdered rather than micronized terfenadine as the former is less soluble than the latter form. A chewable tablet composition also contains a lubricant so that the composition can be compressed into a tablet. Exemplary lubricants are well-known and include magnesium stearate, stearic acid and high molecular weight polyethylene glycols such as those having molecular weights of about 4000 to about 6000. A lubricant can constitute about 0.25 to about 2 weight percent of a chewable tablet.

As noted previously, the particulate (micronized or powdered) terfenadine and Poloxamer are typically dry-blendedly dispersed into the sorbitol to form a homogeneous material. Using a usual tumbling mixer, blender at a slow speed, this dispersal takes about 5–15 minutes at ambient temperature and pressure as are normally used here. The other ingredients, as desired, are then admixed and the admixture is blended for about another 5–15 minutes or until homogeneity is achieved. In addition, for chewable tablets the lubricant is admixed after the other ingredients have been added and mixed.

Once all of the blending is completed, a free-flowing composition is obtained. The composition itself has preferably a pleasant taste, although whether the taste is pleasant or not is governed by the choice of the worker preparing the composition. The composition, more importantly, is substantially free from the taste of solubilized terfenadine when placed on the human tongue in the composition's dry form, or when tasted within about five minutes of being dispersed in water.

By being "substantially free from the taste of terfenadine" it is meant that an average person on tasting the composition would not detect the usually offensive dissolved terfenadine taste. This definition is meant not to be all-inclusive as some people may be particularly sensitive to the terfenadine taste so that no amount of masking will overcome that offensive taste. In addition, some discriminating palates such as those of chefs and other food experts who are used to discriminating one taste from another may be able to discern the distinctive bitter solubilized terfenadine taste. Generally, most people cannot discern the solubilized terfenadine taste in the completed composition.

The resulting granular composition can be used as is for its antihistaminic effects by simply applying an antihistaminic amount of the composition upon the tongue and permitting the composition to disperse in saliva or with an appropriate drink. An antihistaminic amount of the granular composition can also be dispersed with shaking or stirring in a few milliliters of water, e.g. about 5 to about 15 ml, and administered by drinking the dispersed composition. The composition can also be dispersed in a food such as applesauce, mashed bananas, peanut butter or the like and then ingested as those foods are normally ingested.

A contemplated granular terfenadine oral composition can be packaged for sale in a suitable container or package such as a jar or bottle from which the user measures out his or her own antihistaminic dose, as with an appropriately sized spoon or similar device. More preferably, the granular terfenadine is prepackaged in unit dose form so that each packaged unit contains a single antihistaminic dose as discussed before such as 15, 30, 94 60 mg of terfenadine. In one preferred embodiment, the unit dose is packaged in a tear-open packet from which the unit antihistaminic dose of terfenadine can be poured directly onto the tongue or into water or food as discussed before.

BEST MODE FOR CARRYING OUT THE INVENTION

EXAMPLE 1

Terfenadine Oral Granules

A composition designed to provide 60 mg of terfenadine in 2 g of dry composition was prepared as follows.

The sorbitol INSTANT™, maltodextrin and fructose used in the composition were separately sieved using a #60 U.S. Standard Sieve Screen, and only material that passed through the screen was used.

Micronized terfenadine (30 g) and 15 g of the block co-polymer wetting agent (PLURONIC™ polyol F-68) were mixed slowly in a "V-blender" for about five minutes. Sorbitol INSTANT™ (300 g) was added to the mixture and blended therewith for another five minutes to form a blend of all three components.

Microcrystalline cellulose (30 g; AVICEL™ CL-611) PVP (50 g, KOLLIDON™ K-90) maltodextrin (200 g, MALTRIN™ QD M500) and 375 g of fine, granular fructose were added to the above blend, and blending was continued for another ten minutes to form a homogeneous, dry terfenadine composition that was a free flowing powder.

The blended dry composition was thereafter packaged into 2 g sachets as unit doses.

EXAMPLE 2

Taste Assay

A series of ten compositions was prepared using the general procedures described in Example 1. The resulting dry, powdered terfenadine compositions were then assayed by placing 0.5–2 g of the composition individually into the mouths of two experienced taste assayers. The amount of each sample used was determined based on the amount of terfenadine present in the individual samples so that the total amount of terfenadine remained approximately constant. The composition components are shown below in amounts by weight percent of the total composition. Taste ranking scores from each of the two assayers follow each assay of composition components.

| | Composition Components in Weight Percents | | | | | | | | | |
|---|---|---|---|---|---|---|---|---|---|---|
| Terfenadine, Micronized | 1.5 | 1.5 | 1.5 | 3.0 | 3.0 | 3.0 | 6.0 | 6.0 | 12.0 | 12.0 |
| Microncrystalline Cellulose[1] | 3.0 | 3.0 | 3.0 | 3.0 | 3.0 | 3.0 | 3.0 | 3.0 | 3.0 | 3.0 |
| PVP[2] | 5.0 | 5.0 | 5.0 | 5.0 | 5.0 | 5.0 | 5.0 | 5.0 | 5.0 | 5.0 |
| Block Co-polymer[3] | 1.0 | 1.0 | 1.0 | 1.5 | 1.5 | 1.5 | 4.0 | 4.0 | 10.0 | 10.0 |
| Sorbitol INSTANT ™, fine | 30.0 | 30.0 | 30.0 | 30.0 | 30.0 | 30.0 | 30.0 | 30.0 | 30.0 | 30.0 |
| Sucrose, fine | 39.5 | | 20.0 | 37.5 | | 20.0 | 37.0 | | 20.0 | |
| Maltodextrin[4], fine | 20.0 | 20.0 | 39.5 | 20.0 | 20.0 | 37.5 | 15.0 | 15.0 | 20.0 | 20.0 |
| Fructose, fine | | 39.5 | | | 37.5 | | | 37.0 | | 20.0 |

-continued

| Composition Components in Weight Percents | | | | | | | | | | |
|---|---|---|---|---|---|---|---|---|---|---|
| Assayer #1 | 3 | 2 | 4 | 2 | 3 | 4 | 4 | 3 | 4 | 3 |
| Assayer #2 | 3 | 2 | 3 | 2 | 3 | 4 | 4 | 4 | 5 | 4 |

[1]AVICEL ™ CL-611 was used.
[2]KOLLIDON ™ K-90 was used.
[3]Poloxamer 188 was used.
[4]MALTRIN ™ QD M500 was used.

Numerical taste ranking values were as follows: 1=Excellent; 2=Very good; 3=Good; 4=Satisfactory; 5=Acceptable with slight bitter aftertaste; 6=Acceptable with slight soapy taste and bitter aftertaste; and 8=Bitter/unpleasant.

As is seen from the above results, each of the dry, granular terfenadine-containing compositions was acceptable from a taste standpoint. In contrast, a crushed commercially available terfenadine tablet containing an equal amount of terfenadine provides a taste ranking score of about 6 or 7 under these assay conditions.

EXAMPLE 3

Concentrates and Oral Granules

A series of three and four part terfenadine-containing granule concentrates for oral use were prepared as were further oral granule compositions of greater complexity. These compositions were prepared as discussed in Example 1. A less formal taste testing procedure was followed that utilized only one taste analyzer, but used the scale of Example 2. The compositions and taste test results are provided in the Table below.

TABLE

| Composition Components in Weight Percents | | | | |
|---|---|---|---|---|
| Terfenadine, Powdered | — | 12 | — | 12 |
| Terfenadine, Micronized | 12 | — | 12 | — |
| PVP[1] | — | — | 1 | 1 |
| Block Co-polymer[2] | 10 | 10 | 10 | 10 |
| Sorbitol INSTANT ™ fine | 78 | 78 | 77 | 77 |
| Taste Assay | 4 | 3 | 3 | 2 |

[1]KOLLIDON ™ K-90 was used.
[2]Poloxamer 188 was used.

As is seen from the results in the above, the three and four part granular compositions exhibited a satisfactory taste without further ingredients. It is also seen that use of powdered terfenadine provided improved taste properties as compared to the micronized terfenadine.

EXAMPLE 4

Chewable Tablet

An examplary chewable tablet contemplated herein can have a composition as illustrated in the Table, below.

TABLE

| Ingredient | Weight Percent |
|---|---|
| Terfenadine (Micronizer or Powdered) | 10.00 |
| PVP[1] | 3.00 |
| Block Co-polymer[2] | 1.00 |

TABLE-continued

| Ingredient | Weight Percent |
|---|---|
| Maltodextrin[3], fine | 10.00 |
| Sorbitol, INSTANT ™ | 30.00 |
| Aspartame | 0.50 |
| Mannitol or Xylitol | 44.50 |
| Magnesium Stearate | 0.50 |
| Spray-dried Flavor | 0.50 |

[1]KOLLIDON ™ K-90 was used.
[2]Poloxamer 188 was used.
[3]MALTRIN ™ QD M500 was used.

Here, the terfenadine, block-copolymer, aspartame, spray-dried flavor and PVP are premixed in a cube blender for a time period of ten minutes. The sorbitol INSTANT™ is added, and the resulting admixture is mixed for another ten minute time period. The maltodextrin and mannitol or xylitol are added, and the resulting composition is mixed for a further ten minutes. The magnesium stearate lubricant is then added and mixed into the composition for a further three minutes. The lubricated admixture is then made into tablets by compression to a hardness of 9–12 kg (12–18 Strong Cobb units) using ⅜ inch standard concave punches or an appropriate punch/die set.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A dry, granular terfenadine composition that comprises
   (a) a mixture of:
      (i) about 0.20 to about 25 parts by weight particulate terfenadine and
      (ii) about 0.1 to about 15 parts by weight a polyethylene oxide-polypropylene oxide-polyethylene oxide block copolymer having an HLB number of 24 that is a wetting agent for said terfenadine;
   that are dry-blendedly dispersed into:
   (b) about 10 to about 80 parts by weight spray-dried sorbitol particles that are loosely packed, randomly oriented filamentary crystals having pores that entrap said terfenadine particles and wetting agent upon said dry-blended dispersal, said components being further dry blended with
   (c) about 0.5 to about 10 parts by weight dry polyvinylpyrrolidone;
   (d) about zero to about 5 parts by weight dry microcrystalline cellulose mixture that contains about 7 to about 20 weight percent sodium carboxymethylcellulose; and
   (e) a dry flavorant that is absent or present in an amount sufficient to provide a desired taste to said powder;
   said composition being free-flowing and is substantially free from the taste of solubilized terfenadine when placed on the human tongue in dry form or when dispersed in water and tasted within about five minutes of said dispersal.

2. The composition according to claim 1 wherein said terfenadine is present at about 2 to about 10 parts by weight, said spray-dried sorbitol is present at about 25 to about 35 parts by weight and said block copolymer is present at about 1 to about 5 parts by weight.

3. The composition according to claim 1 wherein said polyvinylpyrrolidone is present at a weight ratio relative to said spray-dried sorbitol of about 1:10 to about 1:4.

4. The composition according to claim 1 wherein said microcrystalline cellulose mixture is present at a weight ratio relative to said sorbitol of about 1:20 to about 1:8.

5. The composition according to claim 1 wherein said flavorant powder comprises up to about 60 weight percent of said composition.

6. The composition according to claim 5 wherein said flavorant includes a sweetener.

7. The composition according to claim 1 further including a lubricant and where said granules are compressed into a chewable tablet.

8. The composition according to claim 1 wherein said granules are adapted for oral ingestion.

9. A dry, granular terfenadine composition that comprises
 (a) a mixture of:
  (i) about 2 to about 10 parts by weight micronized terfenadine and
  (ii) about 1 to about 5 parts by weight a polyethylene oxide-polypropylene oxide-polyethylene oxide block copolymer having an HLB number of 24 that is a wetting agent for said terfenadine;
 that are dry-blendedly dispersed into:
 (b) about 25 to about 35 parts by weight spray-dried sorbitol particles that are loosely packed, randomly oriented filamentary crystals having pores that entrap said terfenadine particles and wetting agent upon said dry-blended dispersal, said components being further dry blended with
 (c) about 3 to about 7 parts by weight dry polyvinylpyrrolidone;
 (d) about 2 to about 4 parts by weight dry microcrystalline cellulose mixture that contains about 7 to about 20 weight percent sodium carboxymethylcellulose; and
 (e) about 40 to about 60 parts by weight of a dry flavorant in an amount sufficient to provide a desired taste to said powder, said flavorant including a sweetener;
 said composition being free-flowing and substantially free from the taste of solubilized terfenadine when placed on the human tongue in dry form or when dispersed in water and tasted within about five minutes of said dispersal.

10. The composition according to claim 9 in unit dosage form in a package containing an antihistaminic dose of terfenadine.

11. A dry, granular terfenadine composition that comprises (i) particulate terfenadine, (ii) a polyethylene oxide-polypropylene oxide block copolymer having an HLB number of 24 that is a wetting agent for said terfenadine that are dried-blendedly dispersed into (iii) spray-dried sorbitol particles that are loosely packed, randomly oriented filamentary crystals having pores that entrap said particulate terfenadine and wetting agent upon said dry-blended dispersal; the weight ratio of said particulate terfenadine to said block copolymer being about 1:1 to about 1.5:1, and the weight ratio of said terfenadine to said spray-dried sorbitol being about 1:4 to about 1:10;

said composition being free-flowing and substantially free from the taste of solubilized terfenadine when placed on the human tongue in dry form or when dispersed in water and tasted within about five minutes of said dispersal.

12. The composition according to claim 11 that further includes dry-blendedly admixed polyvinylpyrrolidone present in an amount of about 0.5 to about 5 weight percent of the total composition.

13. The composition according to claim 11 containing an antihistaminic dose of terfenadine.

14. The composition according to claim 11 wherein said particulate terfenadine is present at about 8 to about 12 weight percent, said block copolymer is present at about 5 to about 10 weight percent, said spray-dried sorbitol is present at about 35 to about 70 weight percent.

15. The composition according to claim 14 further including about 15 to about 45 weight percent flavorant.

16. The composition according to claim 15 further including about 0.5 to about 5 weight percent polyvinylpyrrolidine.

17. The composition according to claim 15 wherein said flavorant includes maltodextrin.

18. The composition according to claim 14 wherein said particulate terfenadine is powdered terfenadine.

19. The composition according to claim 18 further including a lubricant and wherein said granules are compressed into a chewable tablet.

20. The composition according to claim 14 wherein said granules are adapted for oral ingestion.

\* \* \* \* \*